(12) United States Patent
Shultz et al.

(10) Patent No.: US 6,364,910 B1
(45) Date of Patent: Apr. 2, 2002

(54) METHOD AND APPARATUS FOR USE OF A GLENOID COMPONENT

(75) Inventors: Jason M. Shultz, Syracuse; Kevin T. Stone, Winona Lake, both of IN (US)

(73) Assignee: Biomet, Inc., Warsaw, IN (US)

(*) Notice: Subject to any disclaimer, the term of this patent is extended or adjusted under 35 U.S.C. 154(b) by 0 days.

(21) Appl. No.: 09/903,097

(22) Filed: Jul. 11, 2001

(51) Int. Cl.⁷ .............................. A61F 2/40; A61B 17/88
(52) U.S. Cl. .................. 623/19.13; 623/19.11; 606/96; 606/86
(58) Field of Search .................. 623/16.11, 18.11, 623/19.11, 19.12, 19.13, 23.43; 606/86, 96

(56) References Cited

U.S. PATENT DOCUMENTS

| | | |
|---|---|---|
| 3,694,820 A | 10/1972 | Scales et al. |
| 3,840,904 A | 10/1974 | Tronzo |
| 4,003,095 A | 1/1977 | Gristina |
| 4,045,826 A | 9/1977 | Stroot |
| 4,106,130 A | 8/1978 | Scales |
| 4,550,450 A | 11/1985 | Kinnett |
| D285,968 S | 9/1986 | Kinnett |
| D285,969 S | 9/1986 | Kinnett |
| 4,986,833 A | 1/1991 | Worland |
| 5,030,219 A * | 7/1991 | Matsen, III et al. ...... 606/96 X |
| 5,112,336 A * | 5/1992 | Krevolin et al. ............... 606/96 |
| 5,593,448 A | 1/1997 | Dong |
| 5,723,018 A * | 3/1998 | Cyprien et al. |
| 5,769,856 A * | 6/1998 | Dong et al. .................... 606/96 |
| 5,800,551 A | 9/1998 | Williamson et al. |
| 5,928,285 A * | 7/1999 | Bigliani et al. |

FOREIGN PATENT DOCUMENTS

| | | |
|---|---|---|
| DE | 3917-285 A | 11/1990 |
| FR | 2579-454 A | 10/1986 |
| FR | 2647-670 A | 12/1990 |

* cited by examiner

*Primary Examiner*—Jeffrey A. Smith
(74) *Attorney, Agent, or Firm*—Harness, Dickey & Pierce, P.L.C.

(57) ABSTRACT

A glenoid component for use in shoulder arthroplasty, the glenoid component is adapted to be implanted into a scapula and engaged by a head of a humeral component. The glenoid component has a body with a first articulating surface and a second medial surface opposite said first articulating surface. The first articulating surface adapted to be engaged by the head of the humeral component and the second medial surface is adapted to be secured to the scapula. A plurality of arcuate pegs, each of said arcuate pegs having a first end adapted to engage a cavity formed in the scapula and a second end extend from the medial surface.

24 Claims, 7 Drawing Sheets

METHOD AND APPARATUS FOR USE OF A GLENOID COMPONENT

BACKGROUND OF THE INVENTION

1. Field of the Invention

This invention relates generally to an apparatus and method for shoulder arthroplasty and, more particularly, to a glenoid component and other associated surgical components and instruments for use in shoulder arthroplasty.

2. Discussion of the Related Art

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus is resected and a cavity is created in the intramedullary canal of the host humerus for accepting a humeral component. The humeral component includes a head portion used to replace the natural head of the humerus. Once the humeral component has been implanted, the glenoid cavity positioned at the scapula head may also be resurfaced and shaped to accept a glenoid component. The glenoid component generally includes an articulating surface which is engaged by the head portion of the humeral component.

It is generally known in the art to provide a shoulder joint prosthesis having a glenoid component, as discussed above. However, the current prior art glenoid components along with the associated surgical components and instruments utilized during shoulder arthroplasty suffer from many disadvantages.

For example, since the glenoid component is subject to various types of loading by the head portion of the humeral component, the glenoid component must offer a stable and secure articulating surface. To achieve this, some glenoid components provide pegs which are inserted and cemented into holes bored into the glenoid cavity. However, such existing pegged glenoid components also exhibit several disadvantages. For example, some of the pegged glenoid components utilize up to five pegs to stabilize and secure the glenoid component to the scapula. Such glenoid components increase the amount of bone tissue removed, while also increasing the labor and complexity of the shoulder arthroplasty. Other pegged glenoid components may offer one or two larger diameter pegs which reduces the complexity of the shoulder arthroplasty. However, the larger diameter pegs also requires excess bone tissue to be removed which may not be practical in some patients. Furthermore, the use of one or two pegs may potentially reduce overall stability of the glenoid component, similar to a keeled glenoid.

Additionally, most prior art glenoid components only rely on the keel or pegs to secure the glenoid component to the scapula, via a cement mantle. The keel or pegs may also include grooves or holes which act as an anchor once the keel or pegs are cemented within the glenoid cavity. The medial surface of most glenoid components are thus generally overlooked to enhance cement fixation and are therefore generally smooth. Although, some glenoid components may include a few longitudinal grooves and others may include both grooves and depressions on the medial surface. However, such surface enhancements only utilize or texture a portion of the medial surface, thereby not advantageously using the entire medial surface. Moreover, such glenoid components do not provide for a uniform cement mantle at the medial surface.

What is needed then is a glenoid component and associated surgical components for use in shoulder arthroplasty which does not suffer from the above-mentioned disadvantages. This in turn, will provide a glenoid component which is stable and secure, reduces the overall amount of bone tissue required to be removed, reduces the overall surgical time and complexity, increases overall medial surface area, enhances and increases attachment strength without increasing overall peg diameter, provides a fully enhanced or textured medial surface for enhanced cement fixation and increased overall stability, provides for a uniform cement mantle, and provides increased tensile and shear strength. It is, therefore, an object of the present invention to provide such a glenoid component and associated surgical components for use in shoulder arthroplasty.

SUMMARY OF THE INVENTION

In accordance with the teachings of the present invention, an apparatus and method for shoulder arthroplasty is disclosed. The apparatus and method employs a glenoid component and other associated surgical components for use in the shoulder arthroplasty. In this regard, the glenoid component is adapted to be implanted into a scapula at the glenoid fossa or cavity and engaged by a head portion of a humeral component.

In one preferred embodiment, a glenoid component is used for shoulder arthroplasty such that the glenoid component is adapted to be implanted into a scapula and engaged by a head of a humeral component. The glenoid component includes a body having a first articulating surface and a second medial surface which is opposite to the first articulating surface. The first articulating surface is adapted to be engaged by the head of the humeral component and the second textured medial surface is adapted to be secured to the scapula. A plurality of curved pegs each have a first end adapted to engage a cavity formed in the scapula and a second end extending from the medial surface. Each of the curved pegs is partially defined by four depending sidewalls having a square cross-section.

Use of the present invention provides an apparatus and method for shoulder arthroplasty, and specifically, a glenoid component and associated surgical components for use in shoulder arthroplasty. As a result, the aforementioned disadvantages associated with the currently available glenoid components and associated surgical components for shoulder arthroplasty have been substantially reduced or eliminated.

The present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

The description of the invention is merely exemplary in nature and, thus, variations that do not depart from the gist of the invention are intended to be within the scope of the invention. Such variations are not to be regarded as a departure from the spirit and scope of the invention.

DETAILED DESCRIPTION OF THE PREFERRED EMBODIMENTS

The following description of the preferred embodiments concerning an apparatus and method for shoulder arthroplasty is merely exemplary in nature and is in no way intended to limit the invention, its application, or uses.

Figure 1:
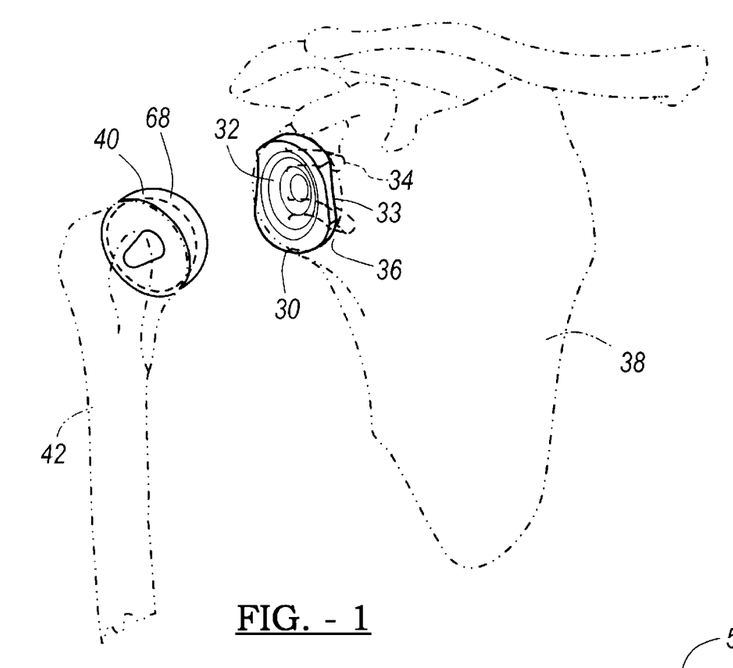
FIG. 1 is a perspective view of the glenoid component according to the teachings of the preferred embodiment of the invention shown implanted in a skeletal structure.

FIG. 1 depicts the components used in the shoulder arthroplasty of the current invention. As shown, the glenoid component 30 has a spherical articulating surface 32 and a medial surface 33. The medial surface 33 has a plurality of arcuate fixation pegs 34, which are used to attach the glenoid component to the resected glenoid cavity 36 of the scapula 38. If a total shoulder arthroplasty is performed, a humeral component 40 is first implanted into the humerus 42 using techniques well known in the art. The humeral component 40 is preferably of the type disclosed in U.S. Pat. No. 4,865,605, which is hereby incorporated by reference, or other suitable conventional humeral components. The glenoid component 30 is designed to allow rotational and transitional movement or rotational movement alone of the head portion 68 of the humeral component with respect to the glenoid component 30.

Figure 2:
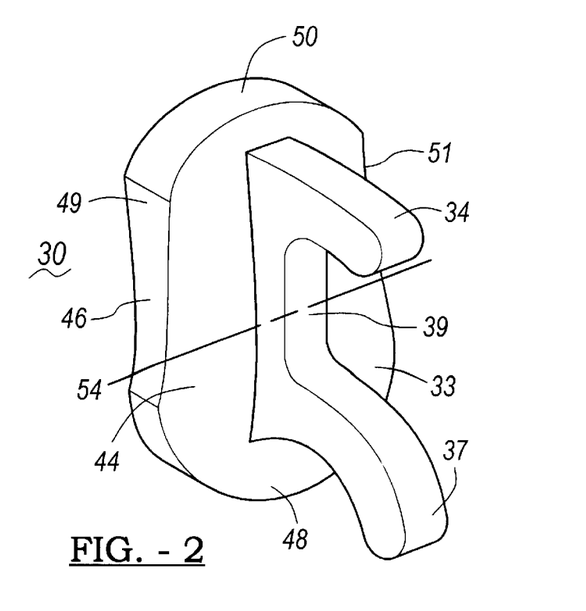
FIG. 2 is a view of the fixation member of glenoid component of FIG. 1.
Figure 3:
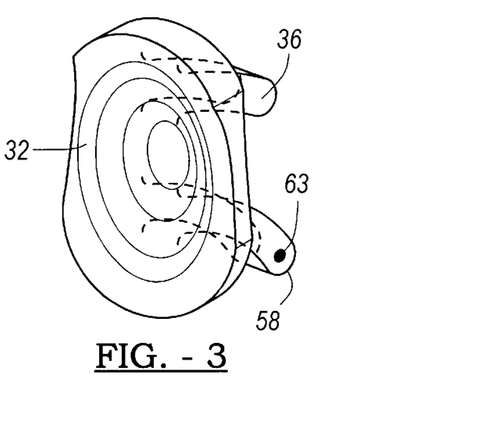
FIGS. 3–4 are an alternate embodiment for the glenoid component of the present invention.

Referring to FIG. 2, a perspective view of a glenoid component 30 according to the teachings of a preferred embodiment of the present invention is shown. The glenoid component 30 includes a body with an articulating and medial surfaces and two arcuate fixation pegs 34 and 37. The glenoid component 30 is preferably made from ultra-high molecular weight polyethylene (UHMWPE) or other suitable implantable material. The dimensions of the glenoid component 30 discussed herein are for a medium sized glenoid component 30. Those skilled in the art will recognize that larger or smaller glenoid components 30 may also be used depending on the patient's size and that the dimensions provided herein are merely for exemplary purposes.

The body 44 is defined by an outer peripheral sidewall 46, a first articulating arcuate or spherical articulating surface 32 (not shown) and a second medial surface 33. The outer peripheral sidewall 46 is generally pear-shaped and includes a curved inferior portion 48 having a radius of about 0.58 inches, a curved superior portion 50 having a radius of about 0.55 inches, a first planar portion 49 and a second planar portion 51. The widest portion of the body 44 is about 1.0 inch and the longest portion of the body is about 1.35 inches. The inferior portion 48 of the peripheral sidewall 46 has a thickness of about 0.15 inches which increases to a thickness of about 0.24 inches at the superior portion 50 such that superior dislocation is minimized.

Figure 4:
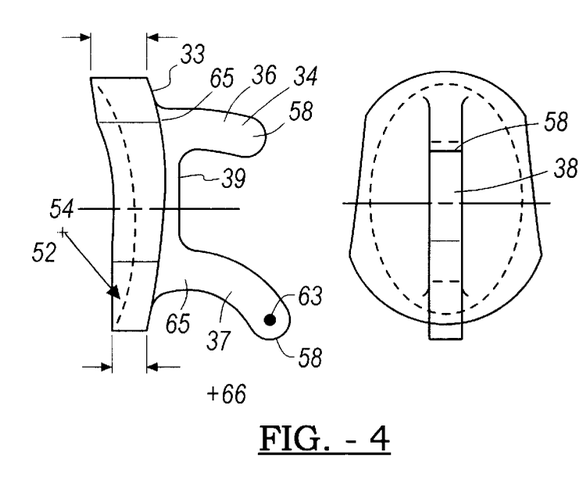

The articulating arcuate or concave spherical articulating surface 32 of the glenoid component 30 is designed to permit both rotational and translational movement of a head of a humeral component. The center 52 of the curvature of the spherical articulating surface 32 is inferior to the center 54 of the glenoid component 30, as shown clearly in FIG. 4a. This offset curvature or sphere provides for the thicker superior region or portion 48. The curvature or sphere has a spherical concave arc defined by a radius of about 1.5 inches from the offset center 52. The offset center 52 is offset by about 0.1 inches from the center 54 of the glenoid component 30.

The medial surface 33 has an overall spherical convex arc defined by a radius of about 3.0 inches from the center 54. Briefly referring to FIG. 5, the medial surface 33 can optionally include an enhanced textured surface over substantially the entire medial surface 33. The medial surface 33 includes a first plurality of parallel grooves 57 positioned substantially perpendicular to a second plurality of parallel grooves 56, similar to a checkerboard or waffle. The grooves 56 and 57 have an angle 59 of about 60°, a depth 62 of about 0.04 inches, and a separation 47 of about 0.075 inches. The grooves 56 and 57 essentially form a plurality of truncated pyramids 61 having a substantially square arcuate top 64 formed by an arc of about 0.03 inches in width and length.

Figure 5:
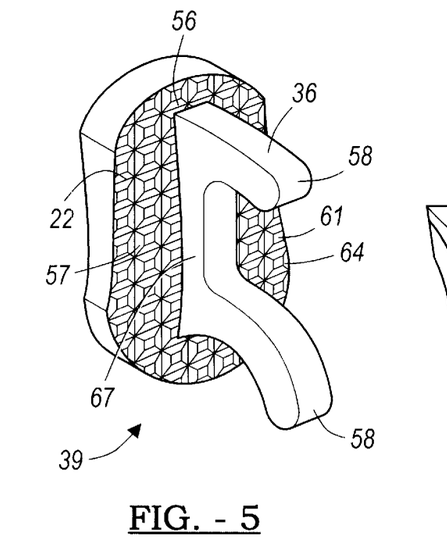
FIGS. 5 and 6, 7 and 8, 9 and 10 are pairs of views which represent alternate peg configurations for the fixation member of the glenoid component of the present invention.
Figure 6:
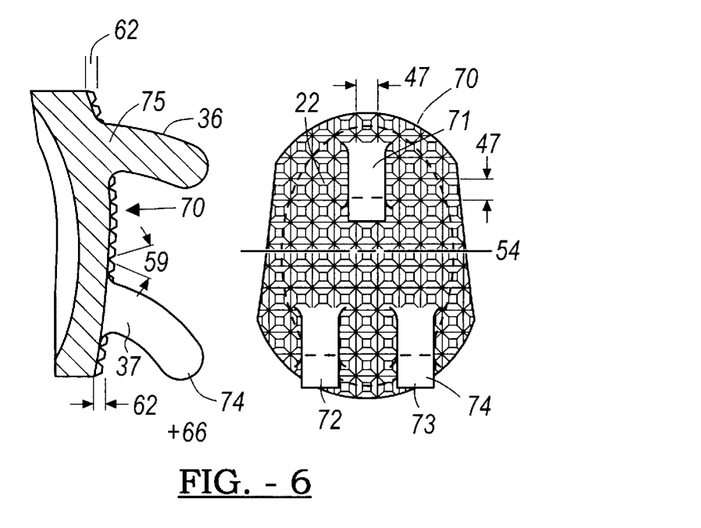

The medial surface 33 may have a textured or waffle surface 22 defined by the truncated pyramids 61 substantially increases the overall medial surface area. As a result, cement adhesion is significantly increased between the medial surface 33 and the scapula 38 due to the waffle texture of surface 33. The angle 60 of the grooves 56 and 57 also enables cement to more easily fill the entire grooves 56 and 57 as compared to grooves having a perpendicular edge. Moreover, both the shear strength and fixation (tensile) strength are greatly increased as compared to conventional smooth glenoid medial surfaces.

One of the arcuate fixation pegs 34 is positioned superior to the center 54 of the glenoid component 30 and the remaining arcuate fixation peg 37 is positioned inferior to the center 54 of the glenoid component 30. As shown in FIG. 2, the arcuate fixation pegs 34, 37 optionally can have a coupling rib 39 which provides for both rotational and translational stability with the minimal volume of arcuate fixation pegs 34, 37, thereby reducing the overall amount of bone tissue removed from the glenoid cavity 36 of the scapula 38.

As shown in FIG. 4a, the arcuate fixation pegs 34, 37 are curved about a fixed rotation point 66. The fixed rotation point 66 allows easy insertion of the glenoid component 30 into the prepared scapula 38. The radius of curvature can be about a point inferior or superior to the glenoid component 30.

Each arcuate fixation peg 34, 37 includes a first end 58 which is inserted into or engages a cavity or hole formed within the glenoid cavity of the scapula and a second end 65 which extends from or is formed integral with the medial surface 33. The first end 58 is semi-circular and the second end 65 has a square cross-section which blends into the optional coupling rib 39 to decrease the overall shear stress of pegs 34, 37. Embedded within the first end 58 of each arcuate fixation peg 34, 37 is a tantalum ball 63. The tantalum balls 63 enable the glenoid component 30 to be easily identified in an x-ray.

The length of each arcuate fixation peg 34, 37 is about 0.37 inches and each are designed to be greater than or equal to twice the length than in width. Therefore, additional bone tissue is not required to be removed, as compared to utilizing a larger diameter peg without the optional coupling rib 39. Moreover, by reducing the amount of bone tissue removed from the glenoid cavity of the scapula 38, the overall strength of the scapula 38 is also increased where the glenoid component 30 engages the scapula 38.

Figure 7:
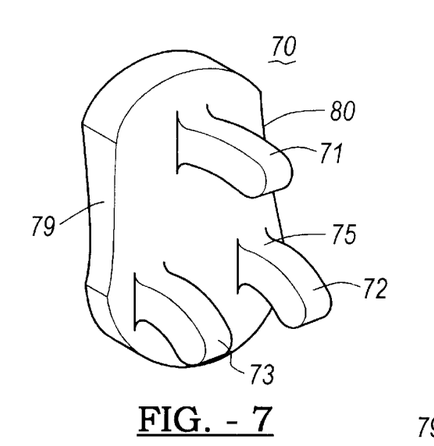

Referring generally to FIGS. 6–10b, a glenoid component 70 is shown having three fixation pegs 71, 72, and 73. The first peg 71 is positioned superior to the center 54 of the glenoid component 30, and the two remaining pegs 72 and 73 are positioned inferior to the center 54 of the glenoid component 30. As shown in FIG. 7, the pegs 71, 72, 73 are positioned to form the corners an isosceles triangle which provides for rotation and translational stability with the minimal amount of pegs 71, 72, 73, thereby reducing the overall amount of bone tissue removed from the glenoid cavity 36 of the scapula 38.

Figure 8:
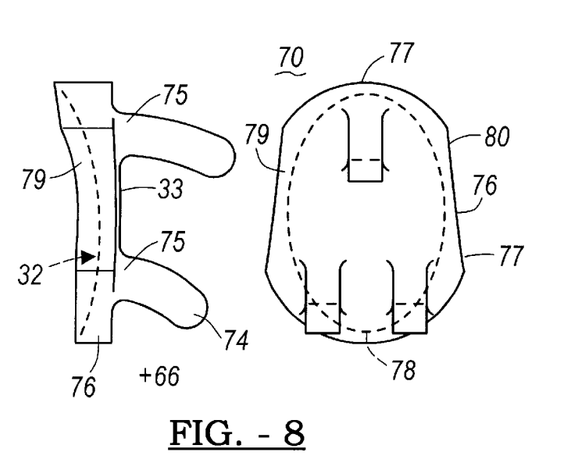
Figure 9:
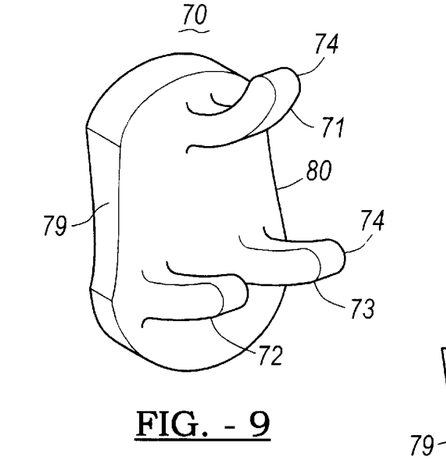

As with the glenoid component depicted in FIGS. 6 through 10, each peg includes a first end 74 which is inserted into or engages the cavity or hole formed in the glenoid cavity of the scapula 38, and a second end 75 which extends from or is formed integral with the medial surface 33. Similarly, each peg 71, 72, 73 is curved about a radius of curvature which is generally inferior to the center 54 of the glenoid component 30 and concentric about a single point. As depicted in FIG. 9, the curved pegs can optionally have a radius of curvature about a line superior to the center 54 of the glenoid 30.

Figure 10:
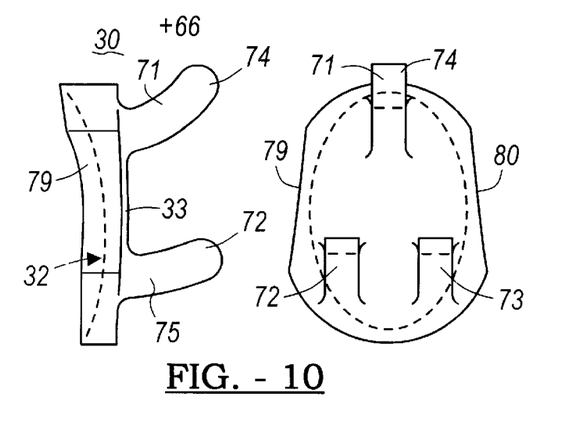

As best seen in FIGS. 8 and 10, the glenoid component 70 is defined by a body 76 having an outer periphery 46, a first articulating or spherical articulating surface 32, and a second medial surface 33. The outer periphery sidewall 46 is generally pear shaped and includes a curved superior portion 77 having a radius of about 0.58 inches, a curved inferior portion 78 having a radius of about 0.55 inches, and first and second planar portions 79, 80.

A method for implanting the glenoid component 30 along with the associated surgical components utilized, will now be described with reference to FIGS. 11–20. Initially, if a total shoulder arthroplasty is performed, a humeral component 40 having a head portion 68 (see FIG. 1) is implanted into the humerus of the patient using techniques well known in the art after the glenoid preparation is complete. Prior to the humeral component 40 implantation into the humerus, glenoid preparation begins. With the glenoid cavity 36 of the scapula 38 exposed, an alignment or pilot hole 84 is first drilled substantially in the center of the glenoid cavity 36 using a 0.157 inch quick release drill bit 80 and a driver 81.

Figure 11:
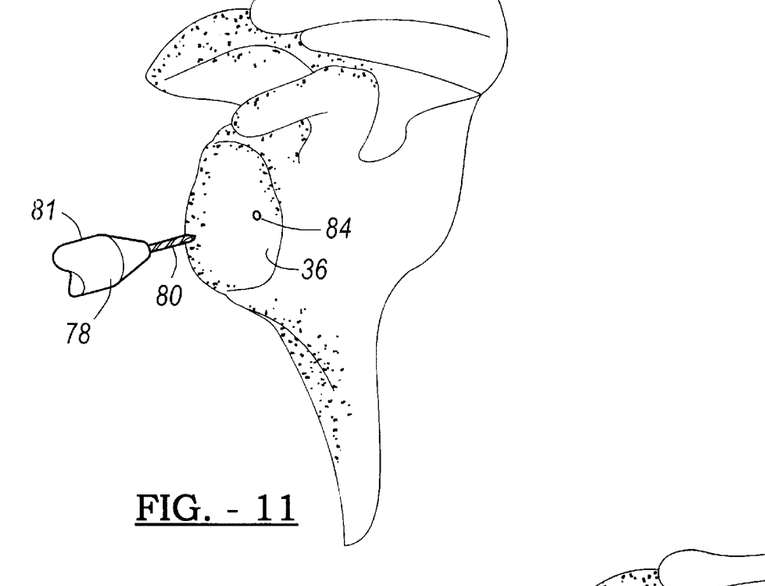
FIGS. 11–20 illustrate a method for implanting the glenoid component using associated surgical components according to the teachings of the preferred embodiment of the present invention.
Figure 12:
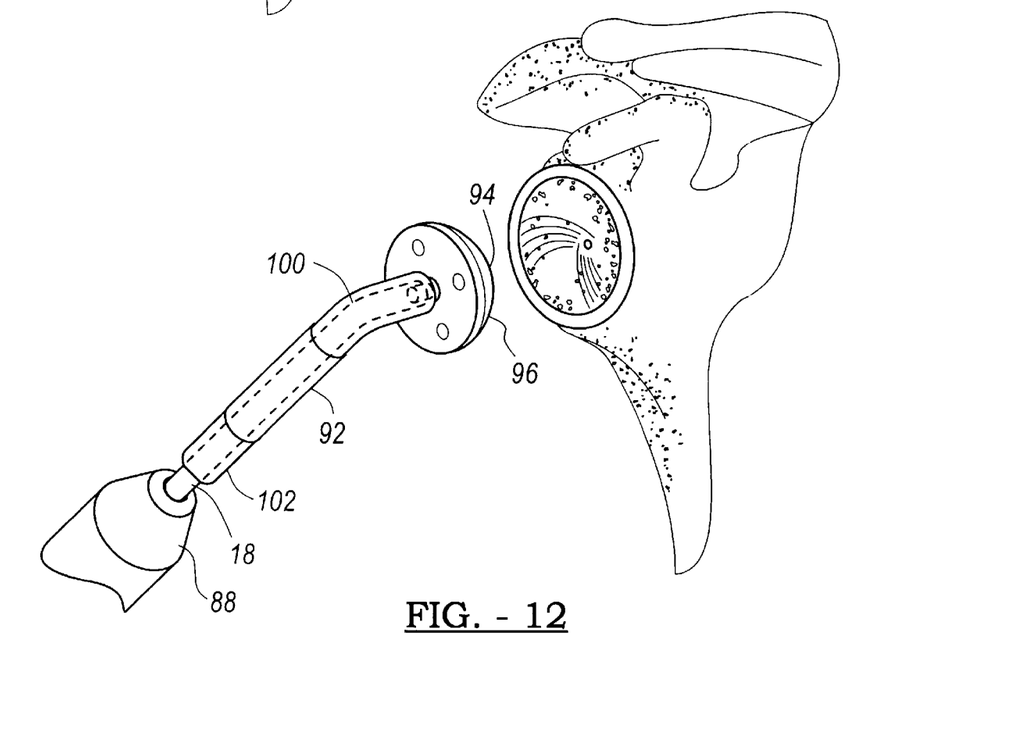

Once the hole 84 is drilled, the glenoid cavity 36 is reamed using a glenoid surface rasp 90 and an angled reamer shaft 92 with driver 88. The glenoid surface rasp 90 may include a guide pin 94 and a roughened spherical surface 96 substantially corresponding to the spherical shape of the medial surface 33 of the glenoid component 30. The guide pin 94 is inserted into the hole 84, and a threaded finger 98 of the rasp 90 rotatably secures the rasp 90 to the angled reamer shaft 92. The angled reamer shaft 92 includes an internal flexible and rotatable drive shaft 100 and an external angled housing 102. The angled reamer shaft 92 permits rasping or drilling in tight glenoid cavities 36. Upon rotating the surface rasp 90, the bone of the glenoid cavity 36 is prepared to mate or conform with the shape of the medial surface 33 of the glenoid component 30.

Figure 13:
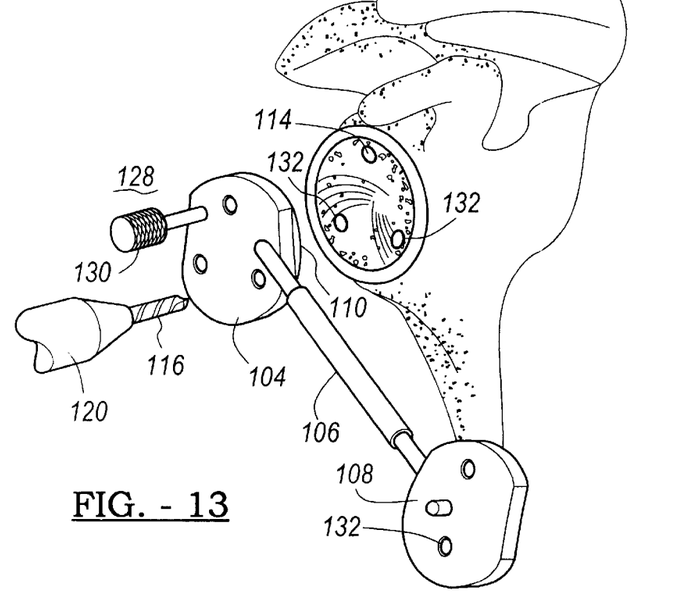

Once the surface of the glenoid cavity 36 has been prepared, a drill guide 104 is employed as a template to locate drill positions for the pegs 71, 72, 73. The drill guide 104 includes a knurled handle 106 and opposing drill templates 108 located on opposite ends of the knurled handle 106. The drill templates 108 are affixed to the handle 106 by a weld or other opposite fixation means. Each drill template 108 has an outer peripheral shape which is substantially similar to the outer peripheral sidewall 46 of the glenoid component 30. Each drill template 108 includes a pointed plug or cruciate 110 located on a spherical medial side 112 of each drill template 108. The cruciate 110 has a larger cross-sectional size than the diameter of the pilot hole 84. The cruciate 110 thereby cuts into the bone tissue as the cruciate 110 is inserted into the pilot hole 84. This action secures the drill guide 104 to the scapula 38, thus preventing rotation of the drill template 108 when drilling the holes for the pegs 71, 72, 73. If the glenoid component is pear-shaped, a right or left hand specific guide 106 is used. For the 3-hole guide, right and left instruments are necessary despite shape of periphery.

Once the cruciate 110 of the drill guide 104 is inserted into the hole 84, thereby securely positioning the drill guide 104 relative to the scapula 38, a superior hole 114 is first drilled using a 0.25 inch diameter drill bit 116 in conjunction with either the angled reamer shaft 92 or a flexible shaft 118. The flexibility of the shaft 118 permits drilling in tight glenoid cavities 36. The flexible shaft 118 includes a quick-connect chuck 120 which receives the quick-connect drill bit 116. The drill bit 116 is sized such that when the chuck 120 of the flexible shaft 118 contacts the drill template 108, the appropriate hole depth for the superior hole 114 is achieved, thereby preventing the surgeon from drilling too deeply into the scapula 38.

Once the superior hole 114 has been drilled, an alignment pin 128 having a knurled shoulder 130 may be inserted through the drill template 108 to further secure the drill guide 104 relative to the scapula 38 prior to drilling the inferior holes 132. The inferior holes 132 are then drilled in the same manner as the superior hole 114. Once the inferior holes 132 are drilled, the alignment pin 128 is removed from the superior hole 114 along with the drill guide 104, thereby exposing the superior hole 114 and the inferior holes 132. It should further be noted that various other drill guides may also be employed.

Once the cavities or holes 114 and 132 have been drilled, a provisional glenoid component (not shown) may be used prior to cementing the glenoid component 30 to verify hole placement, range of motion and appropriate glenoid size. After the proper size glenoid component 30 has been selected, cement is inserted into the superior hole 114, the inferior holes 132 and the pilot hole 84, in addition to being placed on the lateral (or glenoid) surface of the scapula 38 and the medial surface of the glenoid component 30. The pegs 71, 72, 73 of the glenoid component 30 are then inserted into the holes 114 and 132. The glenoid component 30 is then held in place until the cement cures to secure the glenoid component 30 in the scapula 38. The head portion 68 of the humeral component 40 may then engage the spherical articulating surface 32 of the glenoid component 30.

Figure 14:
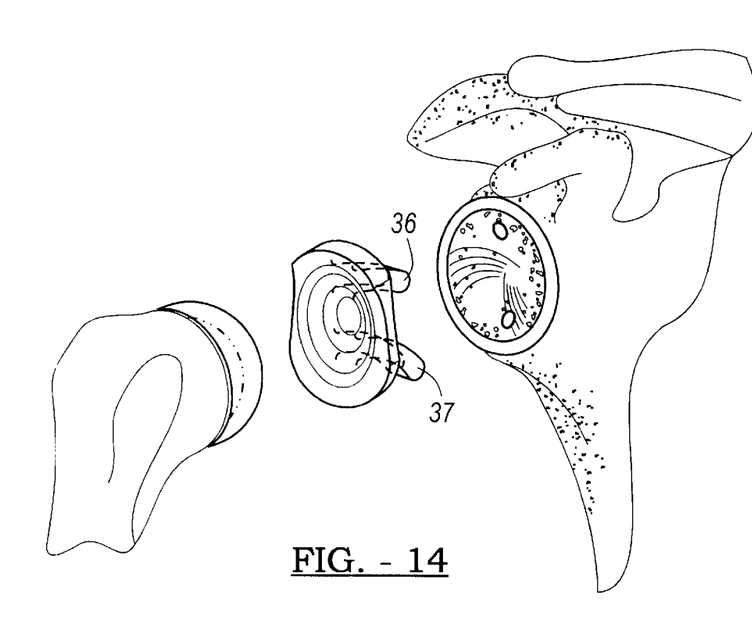

FIG. 14 discloses the implantation of the glenoid component as shown in FIGS. 2–5. As opposed to the insertion procedure as seen in FIGS. 11–13, only two holes are drilled, one inferior and one superior to the guide hole 84.

Figure 15:
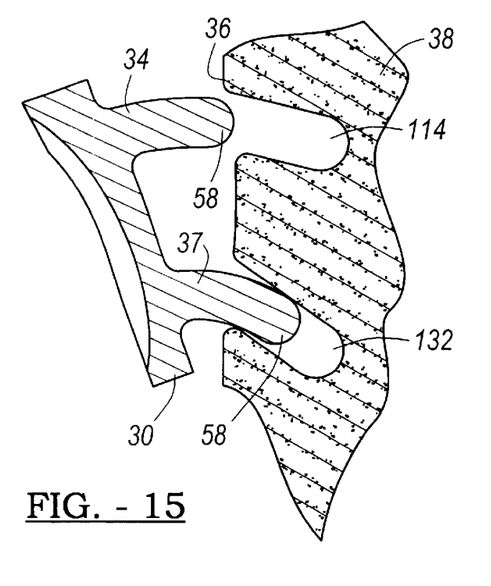
Figure 16:
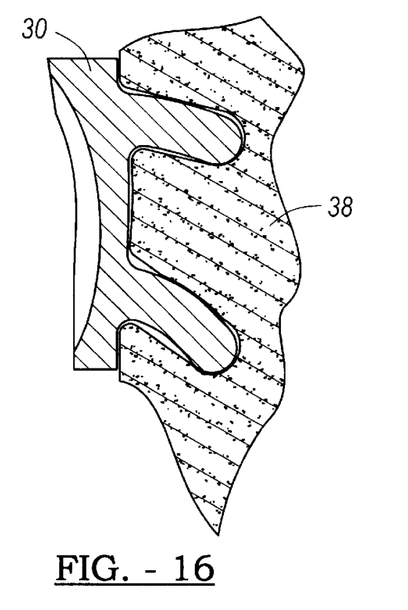
Figure 17:
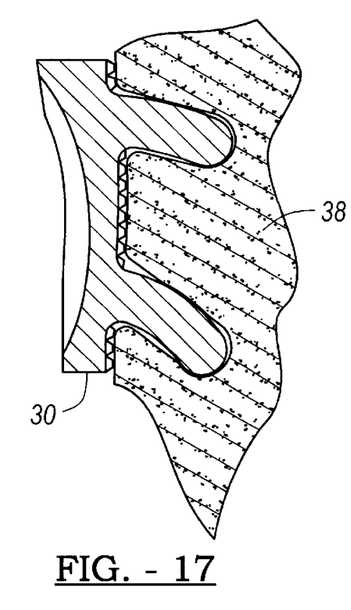

FIGS. 15–17 depict the insertion of the glenoid component as shown in FIGS. 2–5 into the resected scapula 38. As can be seen, the ends 58 of the fixation pegs 34 and 37 are inserted into the angled holes 114 and 132. The glenoid component 30 is rotated about the center of curvature of the arcuate fixation pegs 34 and 37, displacing a small amount bone material. Bone material will be displaced with use of a trial glenoid component or a curved broach or rasp. The glenoid component 30 is rotated until the medial surface 33 engages the resected glenoid cavity 36 of the scapula 38.

Figure 18:
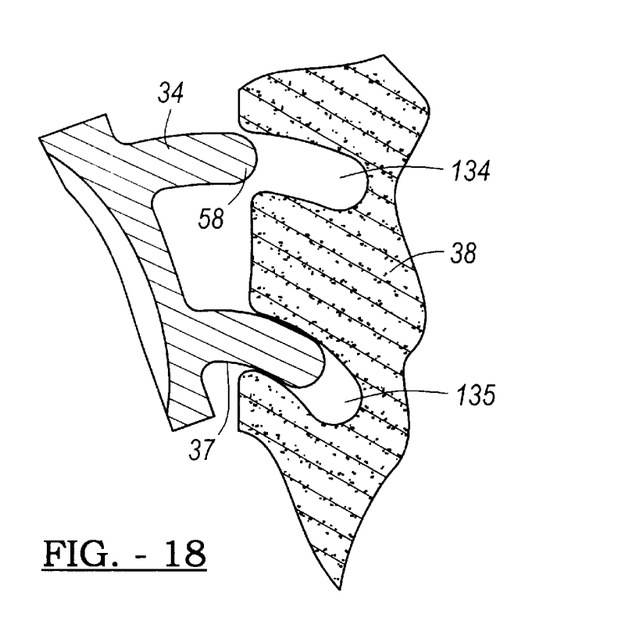
Figure 19:
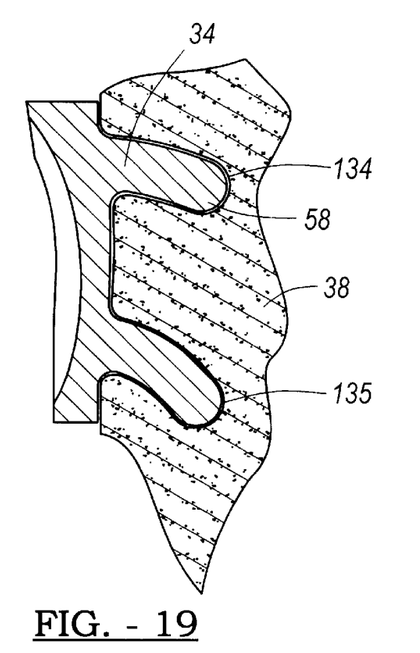
Figure 20:
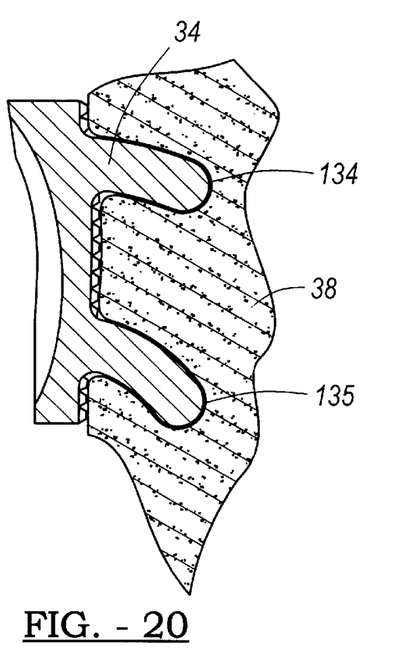

FIGS. 18–20 depict the insertion of the glenoid component as shown in FIGS. 2–5 into the resected scapula 38. As can be seen, the ends 58 of the fixation pegs 34 and 37 are inserted into the curved holes 134 and 135. The curved holes 134 and 135 are formed by using a drill bit/rasp arrangement capable of forming a curved hole. The glenoid component 30 is rotated about the center of curvature of the arcuate fixation pegs 34 and 37, displacing no bone material.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A glenoid component for use in shoulder arthroplasty, said glenoid component adapted to be implanted into a scapula and engaged by a head of a humeral component, said glenoid component comprising:

a body having a first articulating surface and a second medial surface opposite said first articulating surface, said first articulating surface adapted to be engaged by the head of the humeral component and said second medial surface adapted to be secured to the scapula; and a plurality of arcuate pegs, each of said arcuate pegs having a first end adapted to engage a cavity formed in the scapula and a second end extending from said medial surface.

2. The glenoid component as defined in claim 1 wherein said first articulating surface has a spherical concave surface adapted to permit rotational and translational movement of the head of the humeral component.

3. The glenoid component as defined in claim 2 wherein said spherical concave surface has an offset center to provide for a thicker superior portion relative to a thinner inferior portion to reduce superior dislocation of the head of the humeral component.

4. The glenoid components as defined in claim 1 wherein said second medial surface has a spherical convex shape and includes an enhanced textured surface over substantially the entire medial surface.

5. The glenoid component as defined in claim 4 wherein said enhanced textured surface includes a plurality of first parallel grooves positioned substantially perpendicular to a plurality of second parallel grooves to form a plurality of truncated pyramids that substantially increases an overall medial surface area.

6. The glenoid component as defined in claim 1 wherein each of said first ends of said arcuate pegs have a semi-spherical shape.

7. The glenoid component as defined in claim 6 wherein at least one of said second ends of said cylindrical pegs has a square cross-section.

8. The glenoid component as defined in claim 7 wherein each of said arcuate pegs have the same center of curvature.

9. The glenoid component as defined in claim 1 wherein said plurality of arcuate pegs includes a first superior arcuate peg and a pair of second inferior arcuate pegs, each arcuate peg positioned on said second medial surface to form the corner of an isosceles triangle, thereby providing rotational and translational stability with a minimum amount of arcuate pegs.

10. The glenoid component as defined in claim 1 wherein said body is defined by an outer peripheral sidewall which is generally pear-shaped and includes a curved superior portion, a curved inferior portion, a first planar anterior portion and a second planar posterior portion.

11. The glenoid component as defined in claim 1 wherein said arcuate pegs have a center of curvature superior to a center of the glenoid component.

12. The glenoid component as defined in claim 1 wherein the arcuate pegs have a center of curvature inferior to a center of the glenoid component.

13. A set of surgical components for use in shoulder arthroplasty, said set of surgical components comprising:

a glenoid component adapted to be implanted into a scapula and engaged by a head of a humeral component, said glenoid component including, a body having a first spherical articulating surface and a second medial surface, said first spherical articulating surface adapted to permit rotational and translational movement of the head of the humeral component, and a plurality of arcuate pegs, each of said arcuate pegs having a first semi-spherical end adapted to engage a cavity formed in the scapula and a second end extending from said medial portions, each of said arcuate pegs includes flat sidewalls defining a first cross-section.

14. The set of surgical components as defined in claim 13 wherein each of said arcuate pegs includes a center of curvature.

15. The set of surgical components as defined in claim 13 wherein said plurality of arcuate pegs includes a first superior arcuate peg and a pair of second inferior arcuate pegs, each arcuate peg positioned on said second medial surface to form the corners of an isosceles triangle, thereby providing rotational and translational stability with a minimum amount of arcuate pegs.

16. The set of surgical components as defined in claim 13 wherein said body is defined by an outer peripheral sidewall which is generally pear-shaped and includes a curved superior portion, a curved inferior portion, a first planar portion and a second planar portion.

17. The set of surgical components as defined in claim 13 further comprising a drill guide having a plug located on a spherical medial side adapted to prevent translation of said drill guide upon engaging the plug with the scapula.

18. The set of surgical components as defined in claim 17 wherein said drill guide includes a first drill template affixed to a first end of said drill guide and a second drill template affixed to a second end of said drill guide.

19. The set of surgical components as defined in claim 13 further comprising a threaded drill bit having a hole passing therethrough for receipt of a tip of a removal tool.

20. The set of surgical components as defined in claim 13, wherein said arcuate pegs have a center of curvature superior to a center line of the glenoid component.

21. The set of surgical components as defined in claim 13, wherein said arcuate pegs have a center of curvature inferior to a center line of the glenoid component.

22. A set of surgical components as defined in claim 13 wherein said first spherical articulating surface permits only rotational movement of the head of the humeral component.

23. A method for implanting a glenoid component during shoulder arthroplasty, said method comprising the steps of:

drilling a center pilot hole in a glenoid cavity of a scapula;

inserting a guide pin of a glenoid surface rasp into the center pilot hole;

rotating the glenoid surface rasp to prepare a spherical surface on the glenoid cavity;

positioning a drill guide into the pilot hole to secure the drill guide to the scapula;

drilling a plurality of holes in the scapula using a drill template of the drill guide;

providing a glenoid component having a body, a plurality of arcuate pegs, said body having a first articulating surface and a second medial surface, each of said arcuate pegs extending from said medial surface and adapted to engage the hole drilled in the scapula;

inserting cement into the plurality of holes drilled in the glenoid cavity, on the spherical surface of the glenoid cavity and on the second medial surface of the glenoid component; and inserting the glenoid component into the glenoid cavity of the scapula by inserting the plurality of arcuate pegs into the plurality of holes and securing the second medial surface to the spherical surface of the glenoid cavity.

24. The method as defined in claim 23 wherein the step of inserting the glenoid component into the glenoid cavity includes the step of rotating the glenoid component about the center of curvature of the arcuate pegs after the pegs are inserted into the plurality of holes.

* * * * *